(12) United States Patent
Allan et al.

(10) Patent No.: US 8,328,711 B2
(45) Date of Patent: Dec. 11, 2012

(54) SELECTABLE MULTI-LUMEN BRACHYTHERAPY DEVICES AND METHODS

(75) Inventors: Donna Allan, Bedford, NH (US); Greg Amante, Holliston, MA (US)

(73) Assignee: Cytyc Corporation, Marlborough, MA (US)

( * ) Notice: Subject to any disclaimer, the term of this patent is extended or adjusted under 35 U.S.C. 154(b) by 1362 days.

(21) Appl. No.: 11/959,227

(22) Filed: Dec. 18, 2007

(65) Prior Publication Data
US 2009/0156880 A1 Jun. 18, 2009

(51) Int. Cl.
*A61N 5/00* (2006.01)
(52) U.S. Cl. .......................................................... 600/3
(58) Field of Classification Search ................. 600/1–8
See application file for complete search history.

(56) References Cited

U.S. PATENT DOCUMENTS

| | | |
|---|---|---|
| 3,324,847 A | 6/1967 | Zoumboulis |
| 3,872,856 A | 3/1975 | Clayton |
| 4,350,169 A | 9/1982 | Dutcher et al. |
| 4,417,576 A | 11/1983 | Baran |
| 4,706,652 A | 11/1987 | Horowitz |
| 4,754,745 A | 7/1988 | Horowitz |
| 4,763,642 A | 8/1988 | Horowitz |
| 4,821,725 A | 4/1989 | Azam et al. |
| 4,867,741 A | 9/1989 | Portnoy |
| 5,015,247 A | 5/1991 | Michelson |
| 5,084,001 A | 1/1992 | Van't Hooft et al. |
| 5,084,015 A | 1/1992 | Moriuchi |
| 5,106,360 A | 4/1992 | Ishiwara et al. |
| 5,112,303 A | 5/1992 | Pudenz et al. |
| 5,152,747 A | 10/1992 | Olivier |
| 5,236,410 A | 8/1993 | Granov et al. |
| 5,422,926 A | 6/1995 | Smith et al. |
| 5,484,384 A | 1/1996 | Fearnot |
| 5,520,646 A | 5/1996 | D'Andrea |
| 5,562,594 A | 10/1996 | Weeks |
| 5,566,221 A | 10/1996 | Smith et al. |
| 5,653,683 A | 8/1997 | D'Andrea |
| 5,720,717 A | 2/1998 | D'Andrea |
| 5,724,400 A | 3/1998 | Swerdloff et al. |
| 5,741,253 A | 4/1998 | Michelson |
| 5,800,333 A | 9/1998 | Liprie |
| 5,803,895 A | 9/1998 | Kronholz et al. |

(Continued)

FOREIGN PATENT DOCUMENTS
DE 25 39 553 3/1977
(Continued)

OTHER PUBLICATIONS

International Preliminary Report on Patentability and Written Opinion from related PCT Application No. PCT/US2008/086641 dated Jun. 22, 2010.

(Continued)

*Primary Examiner* — Christine Matthews (57) ABSTRACT

A brachytherapy treatment device includes at least one tubular insertion member and an expandable member. The tubular insertion member has proximal and distal ends and at least one radiation source lumen disposed along its length and branching at the distal end to provide a plurality of selectable radiation source lumens each configured to receive a radiation source. The expandable member is disposed on and surrounding the distal end of the tubular insertion member. In another embodiment, a brachytherapy treatment device may also include a plurality of selectable radiation source lumens forming an arcuate shape with respect to the longitudinal axis. Additional brachytherapy treatment devices and methods for performing brachytherapy and for forming an asymmetric radiation dosing profile are also disclosed.

18 Claims, 4 Drawing Sheets

U.S. PATENT DOCUMENTS

| | | | |
|---|---|---|---|
| 5,851,182 | A | 12/1998 | Sahadevan |
| 5,863,284 | A | 1/1999 | Klein |
| 5,913,813 | A | 6/1999 | Williams et al. |
| 6,036,631 | A | 3/2000 | McGrath et al. |
| 6,050,930 | A | 4/2000 | Teirstein |
| 6,234,952 | B1 | 5/2001 | Liprie |
| 6,267,775 | B1 | 7/2001 | Clerc et al. |
| 6,306,074 | B1 | 10/2001 | Waksman et al. |
| 6,413,204 | B1 | 7/2002 | Winkler et al. |
| 6,416,457 | B1 | 7/2002 | Urick et al. |
| 6,458,070 | B1 | 10/2002 | Waksman et al. |
| 6,482,142 | B1 | 11/2002 | Winkler et al. |
| 6,558,390 | B2 | 5/2003 | Cragg |
| 6,607,477 | B1 | 8/2003 | Longton et al. |
| 6,616,629 | B1 | 9/2003 | Verin et al. |
| 6,685,618 | B2 | 2/2004 | Tam et al. |
| 2003/0153803 | A1 | 8/2003 | Harmon |
| 2005/0124843 | A1 | 6/2005 | Singh |
| 2006/0100475 | A1 | 5/2006 | White et al. |
| 2007/0167666 | A1 | 7/2007 | Lubock et al. |
| 2007/0191667 | A1 | 8/2007 | Lubock et al. |
| 2007/0270627 | A1 | 11/2007 | Cutrer et al. |
| 2008/0221384 | A1 | 9/2008 | Chi Sing et al. |

FOREIGN PATENT DOCUMENTS

| | | |
|---|---|---|
| EP | 0 340 881 | 10/1992 |
| EP | 0 867 200 | 9/1998 |
| EP | 1 618 924 | 1/2006 |
| WO | WO92/10932 | 7/1992 |
| WO | WO93/09724 | 5/1993 |
| WO | WO97/19723 | 6/1997 |
| WO | WO99/11325 | 3/1999 |
| WO | WO99/33515 | 7/1999 |
| WO | WO99/42163 | 9/1999 |
| WO | WO01/43826 | 6/2001 |
| WO | WO2007/143560 | 12/2007 |
| WO | WO2008/067557 | 6/2008 |
| WO | WO2009/079170 | 6/2009 |

OTHER PUBLICATIONS

International Search Report and Written Opinion from related PCT Application No. PCT/US2010/023454 dated May 7, 2010.

International Search Report and Written Opinion from related PCT Application No. PCT/US2010/023461 dated Jun. 1, 2010.

International Search Report and Written Opinion from related PCT Application No. PCT/US2010/033370 dated Jul. 30, 2010.

International Search Report and Written Opinion from related PCT Application No. PCT/US2010/033373 dated Aug. 9, 2010.

International Search Report from related PCT Application No. PCT/US2008/086641 dated Apr. 15, 2009.

Nath, Ph.D. et al., Development of an 241 Am Applicator for Intracavitary Irradiation of Gynecologic Cancers, I.J. Radiation Oncology Bio. Phys., May 1988, vol. 14, p. 969-978.

SELECTABLE MULTI-LUMEN BRACHYTHERAPY DEVICES AND METHODS

TECHNICAL FIELD

This technology relates generally to brachytherapy devices and methods for use in treating proliferative tissue disorders.

BACKGROUND

Body tissues subject to proliferative tissue disorders, such as malignant tumors, are often treated by surgical resection of the tumor to remove as much of the tumor as possible. Unfortunately, the infiltration of the tumor cells into normal tissues surrounding the tumor may limit the therapeutic value of surgical resection because the infiltration can be difficult or impossible to treat surgically. Radiation therapy may be used to supplement surgical resection by targeting the residual tumor margin after resection, with the goal of reducing its size or stabilizing it. Radiation therapy may be administered through one of several methods, or a combination of methods, such as interstitial or intercavity brachytherapy. Brachytherapy may also be administered via electronic brachytherapy using electronic sources, such as x-ray sources, for example.

Brachytherapy is radiation therapy in which the source of radiation is placed in or close to the area to be treated, such as within a cavity or void left after surgical resection of a tumor. Brachytherapy may be administered by implanting or delivering a spatially confined radioactive material to a treatment site, which may be a cavity left after surgical resection of a tumor. For example, brachytherapy may be performed by using an implantable device (e.g., catheter or applicator) to implant or deliver radiation sources directly into the tissue(s) or cavity to be treated. During brachytherapy treatment, a catheter may be inserted into the body at or near the treatment site and subsequently a radiation source may be inserted through the catheter and placed at the treatment site.

Brachytherapy is typically most appropriate where: 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. Interstitial and/or intercavity brachytherapy may be useful for treating malignant brain and breast tumors, among other types of proliferative tissue disorders.

There are two basic types of brachytherapy, high dose rate and low dose rate. These types of brachytherapy generally include the implantation of radioactive "seeds," such as palladium or iodine, into the tumor, organ tissues, or cavity to be treated. Low dose rate (LDR) brachytherapy refers to placement of multiple sources (similar to seeds) in applicators or catheters, which are themselves implanted in a patient's body. These sources are left in place continuously over a treatment period of several days, after which both the sources and applicators are removed. High dose rate brachytherapy (HDR) uses catheters or applicators similar to those used for LDR. Typically, only a single radiation source is used, but of very high strength. This single source is remotely positioned within the applicators at one or more positions, for treatment times which are measured in seconds to minutes. The treatment is divided into multiple sessions ('fractions'), which are repeated over a course of a few days. In particular, an applicator (also referred to as an applicator catheter or treatment catheter) is inserted at the treatment site so that the distal region is located at the treatment site while the proximal end of the applicator protrudes outside the body. The proximal end is connected to a transfer tube, which in turn is connected to an afterloader to create a closed transfer pathway for the radiation source to traverse. Once the closed pathway is complete, the afterloader directs its radioactive source (which is attached to the end of a wire controlled by the afterloader) through the transfer tube into the treatment applicator for a set amount of time. When the treatment is completed, the radiation source is retracted back into the afterloader, and the transfer tube is disconnected from the applicator.

A typical applicator catheter comprises a tubular member having a distal portion which is adapted to be inserted into the patient's body, and a proximal portion which extends outside of the patient. A balloon is provided on the distal portion of the tubular member which, when placed at the treatment site and inflated, causes the surrounding tissue to substantially conform to the surface of the balloon. In use, the applicator catheter is inserted into the patient's body, for instance, at the location of a surgical resection to remove a tumor. The distal portion of the tubular member and the balloon are placed at, or near, the treatment site, e.g. the resected space. The balloon is inflated, and a radiation source is placed through the tubular member to the location within the balloon.

Several brachytherapy devices are described in U.S. Provisional Patent Application 60/870,690, entitled "Brachytherapy Device and Method," and U.S. Provisional Patent Application 60/870,670, entitled "Asymmetric Radiation Dosing Devices and Methods," both filed on Dec. 19, 2006, which are both commonly owned with the present application, and with copending U.S. patent application entitled "Asymmetric Radiation Dosing Devices and Methods," filed on or about Dec. 18, 2007, U.S. Pat. Nos. 5,913,813, and 6,482,142, all of which are hereby incorporated by reference herein in their entireties.

The dose rate at a target point exterior to a radiation source is inversely proportional to the square of the distance between the radiation source and the target point. Thus, previously described applicators, such as those described in U.S. Pat. No. 6,482,142, issued on Nov. 19, 2002, to Winkler et al., are symmetrically disposed about the axis of the tubular member so that they position the tissue surrounding the balloon at a uniform or symmetric distance from the axis of the tubular member. In this way, the radiation dose profile from a radiation source placed within the tubular member at the location of the balloon is symmetrically shaped relative to the balloon. In general, the amount of radiation desired by a treating physician is a certain minimum amount that is delivered to a region up to about two centimeters away from the wall of the excised tumor, i.e. the target treatment region. It is desirable to keep the radiation that is delivered to the tissue in this target tissue within a narrow absorbed dose range to prevent overexposure to tissue at or near the balloon wall, while still delivering the minimum prescribed dose at the maximum prescribed distance from the balloon wall (i.e. the two centimeter thickness surrounding the wall of the excised tumor).

However, in some situations, such as a treatment site located near sensitive tissue like a patient's skin, the symmetric dosing profile may provide too much radiation to the sensitive tissue such that the tissue suffers damage or even necrosis. In such situations, the dosing profile may cause unnecessary radiation exposure to healthy tissue or it may damage sensitive tissue, or it may not even be possible to perform a conventional brachytherapy procedure.

To alleviate some of these problems associated with prior applicators, an asymmetric dosing profile is produced by shaping or locating the radiation source so as to be asymmetrically placed with respect to the longitudinal axis of the balloon. In an alternative approach, the applicator is provided with asymmetric radiation shielding located between the radiation source and the target tissue.

However, asymmetrically placing the radiation source decreases the radiation dosing profile in certain directions, but correspondingly increases the radiation dosing profile in the other directions. Some devices may not allow for adjustment of the amount of asymmetry and/or the resulting radiation dosing profile shape. Accordingly, there remains a need for additional methods and devices which can provide an asymmetric radiation dosing profile having a predetermined orientation during brachytherapy procedures.

SUMMARY

Brachytherapy treatment devices and methods are disclosed herein. The brachytherapy treatment devices and methods disclosed herein may be oriented to create an asymmetric radiation dosing profile relative to an inner boundary of target tissue at a treatment site. The asymmetric radiation dosing profile functions to protect certain sensitive tissues from receiving an undesirably high dose of radiation while still allowing the remainder of target tissue at a treatment site to receive a prescribed therapeutic dosage of radiation treatment.

In one embodiment, a brachytherapy treatment device has a tubular insertion member and an expandable member. The tubular insertion member has a proximal end and a distal end. The tubular insertion member has at least one radiation source lumen disposed along its length and branching at the distal end to provide a plurality of selectable radiation source lumens each configured to receive a radiation source. The expandable member is disposed on and surrounds the distal end of the tubular insertion member.

In another embodiment, a brachytherapy treatment device includes a tubular insertion member and an expandable member. The at least one tubular insertion member has a longitudinal axis, a proximal end and a distal end. The tubular insertion member has a plurality of selectable radiation source lumens each configured to receive a radiation source, wherein at least one of the plurality of selectable radiation source lumens forms an arcuate shape with respect to the longitudinal axis. The expandable member is disposed on and surrounds the distal end of the at least one tubular insertion member.

In one embodiment, a method of performing brachytherapy includes: i) inserting a brachytherapy treatment device at a treatment site, the device comprising: a tubular insertion member having a proximal end and a distal end, the tubular insertion member having at least one radiation source lumen disposed along its length and branching at the distal end to provide a plurality of selectable radiation source lumens each configured to receive a radiation source; and an expandable member disposed on and surrounding the distal end of the tubular insertion member; ii) deploying the expandable member at the treatment site; and iii) selecting at least one of the plurality of selectable radiation source pathways to position a radiation source within at least one of the plurality of selectable radiation source pathways.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Brachytherapy treatment devices and methods disclosed herein provide a radiation dosing profile which may be oriented in any number of configurations. In some embodiments the radiation dosing profile generated may be asymmetrical to protect sensitive tissues while still allowing target tissues to receive an appropriate therapeutic dose of radiation. Referring now to FIGS. 1-9, like numerals indicate like features throughout the drawing figures shown and described herein.

Figure 1:
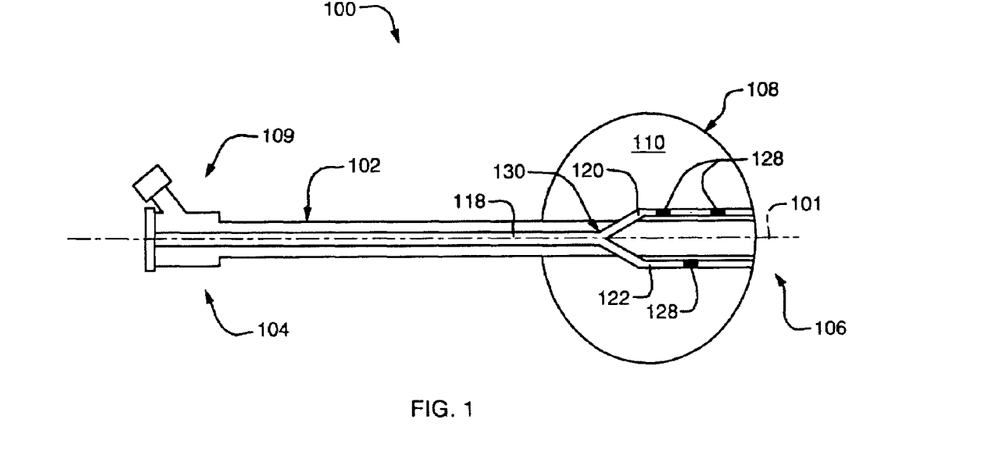
FIG. 1 illustrates a cross-section of an exemplary brachytherapy device having a plurality of selectable radiation source lumens.

FIG. 1 illustrates a first embodiment of a brachytherapy treatment device 100 having a tubular insertion member 102 and an expandable member 108. A brachytherapy applicator or treatment device 100 (also commonly referred to as an applicator catheter or treatment catheter) may comprise at least one elongated tubular insertion member 102 having a longitudinal axis 101 extending its length between a proximal end 104 and a distal end 106. The distal end 106 of the tubular insertion member 102 is adapted to be inserted into a patient's body and the proximal end 104 is adapted to extend outside of the patient's body. The tubular insertion member 102 should be rigid enough to provide an easy insertion profile for a surgeon, while still being soft and flexible enough to be comfortable for a patient during treatment. In some embodiments, a device 100 may include a plurality of tubular insertion members 102. Device 100 may be formed of material capable of being visualized or detected using external imaging equipment, such as materials visualizable using ultrasound, x-ray, or MRI.

The tubular insertion member 102 may be formed of a flexible material, including without limitation various plastic or elastomeric polymers and/or other suitable materials. The tubular insertion member 102 should be flexible and soft enough that it conforms to surrounding tissue and easily bends when force is applied, such as by movement of the patient's body, making the tubular insertion member 102 more comfortable. The tubular insertion member 102 may further comprise a malleable element (not shown) adapted to confer a shape upon at least a portion of its length. The walls of the tubular insertion member 102 may be substantially impermeable to fluids, except where there are apertures and/or openings disposed within the walls of the tubular insertion member 102.

Additionally, the at least one tubular insertion member may be composed of different materials and/or combinations of materials having different properties in order to provide varying degrees of radiation absorption or attenuation. For example, thick or dense materials may be used to provide more attenuation, which can be localized or directed to produce a desired dosing pattern. Additionally, the at least one tubular insertion member 102 may be formed of a composite of more than one material or thickness in order to provide varying degrees of attenuation. For example, the at least one tubular insertion member 102 may be thicker in the direction of sensitive tissue in order to reduce or even shield the radiation dose applied to the sensitive tissue and/or the shield may be thinner in the opposite direction in order to provide a higher radiation dose to the target tissue.

As shown in FIG. 1, the device 100 may further comprise an expandable member 108 disposed on and surrounding the distal end 106 of the at least one tubular insertion member 102 and having an inner surface defining a three-dimensional volume 110. The internal volume 110 defined by the expandable member 108, when inflated, may be substantially similar to the volume of the cavity to substantially fill the cavity and help provide a substantially uniform and symmetrical boundary. The expandable member 108 may be any device which can be controllably expanded and contracted to retract surrounding tissue, such as a balloon, bladder, or other device.

The expandable/member 108 may be formed of a variety of different materials, such as biocompatible polymers. Some exemplary biocompatible polymers may include silastic rubbers, polyurethanes, polyethylene, polypropylene, and polyester, just to name a few examples. The walls of the expandable member 108 will be formed of a radiation transparent material to allow radiation to pass through the walls of the expandable member 108 to treat the tissue of the cavity surrounding the expandable member 108. In some embodiments, it may be desirable to use one or more expandable members 108 or a double-walled member to minimize the risk of fluid leakage from the expandable member 108 into a patient, such as may occur if one expandable member 108 becomes punctured.

The tubular insertion member 102 and/or main lumen 118 may further comprise an inflation lumen, such as a balloon inflation tube, disposed within the wall of the tubular insertion member 102 or the main lumen 118 and fluidly coupling the expandable member 108 and the proximal end 104 of the tubular insertion member 102. The inflation lumen (now shown) provides a fluid pathway, allowing the expandable member 108 to be remotely expanded/inflated and contracted/deflated from a location at the proximal end 104 of the tubular insertion member 102, such as by a user or machine. In some embodiments, the main lumen 118 may comprise multiple inflation lumens for inflating multiple expandable members 108.

The device 100 may further comprise a hub 109 disposed on the proximal end 104. Hub 106 may contain one or more ports operably coupled to the radiation source lumen 118 and to the expandable member 108 via an inflation lumen. Hub 106 is configured to remain outside of a patient during treatment and provides access to the radiation source lumen 118 and the expandable member 108 during treatment.

As shown in FIG. 1, the tubular insertion member 102 may also include at least one radiation source lumen (or main lumen) 118 disposed along its length. The radiation source lumen 118 extends between and operably couples the proximal 104 and distal 106 ends of the tubular insertion member 102. The radiation source lumen 118 may be a radiation source pathway configured to receive a radiation source and provide a pathway for positioning a radiation source at any of the radiation source positions 128 (shown in FIG. 1) within the expandable member 108.

The radiation source lumen 118 within tubular insertion member 102 branches at the distal end 106, as shown in FIG. 1. The branch or bifurcation 130 within radiation source lumen 118 divides the radiation source lumen 118 into at least one (or a plurality) of selectable radiation source lumens 120, 122. The branch 130 provides a plurality of selectable radiation source lumens 120, 122 each configured to receive a radiation source. The radiation source lumen 118 and the selectable radiation source lumens 120, 122 are operably coupled and adapted to provide continuous radiation source pathways between the proximal end 104 and the distal end 106.

Because the plurality of selectable radiation source lumens 120, 122 are configured to extend the radiation source pathway of the radiation source lumen 118, the angle of branching or divergence(s) at the bifurcation 130 may be gradual to accommodate a flexible wire having a minimal radius of curvature. In some embodiments, the bifurcation 130 may comprise a gently sloped or ramped portion which more gradually changes radiation source lumen 118 into one of the plurality of selectable radiation source lumens 120, 122. In some implementations, there may be more than one bifurcation 130. It may also be advantageous to have each of the plurality of selectable radiation source lumens 120, 122 branch 130 off of the radiation source lumen 118 at different positions along the radiation source lumen 118.

Other embodiments for easing insertion of a flexible wire through radiation source pathway 118 and controlling direction of a flexible wire into one of the plurality of selectable radiation source lumens 120, 122 are also contemplated herein. In yet additional embodiments, the branch 130 may simply comprise a change in the pathway or direction of radiation source lumen 118. The branch or bifurcation 130 may be operably coupled to a pathway select mechanism to provide access to a predetermined one or more of the plurality of selectable radiation source lumens 120, 122 at the distal end 106 of the device 100, as will be described below in more detail.

Figure 2:
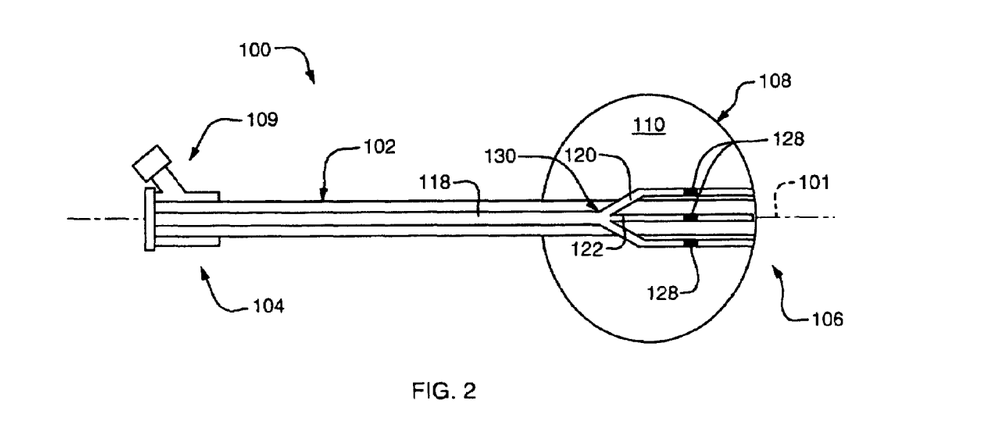
FIG. 2 illustrates a cross-section of an exemplary brachytherapy device having a plurality of selectable radiation source lumens.

FIG. 2 illustrates an exemplary embodiment of a brachytherapy treatment device having a tubular insertion member 102 having at least one radiation source lumen 118 branching at bifurcation 130 to provide three selectable radiation source lumens 120, 122, 124. As shown in FIG. 2, one of the plurality of selectable radiation source lumens 122 may be disposed along the longitudinal axis 101. In this embodiment, the selectable radiation source lumen 122 may be a continuous extension of radiation source lumen 118 (both being disposed along longitudinal axis 101), although the selectable radiation source lumen 122 may have a different diameter than that of radiation source lumen 118. In the embodiment shown in FIG. 2, selectable radiation source lumen 122 may have a smaller diameter than that of radiation source lumen 118. With continuing reference to FIG. 2, two of the plurality of selectable radiation source lumens 120, 124 may be disposed to be off-center or offset from longitudinal axis 101.

Figure 3:
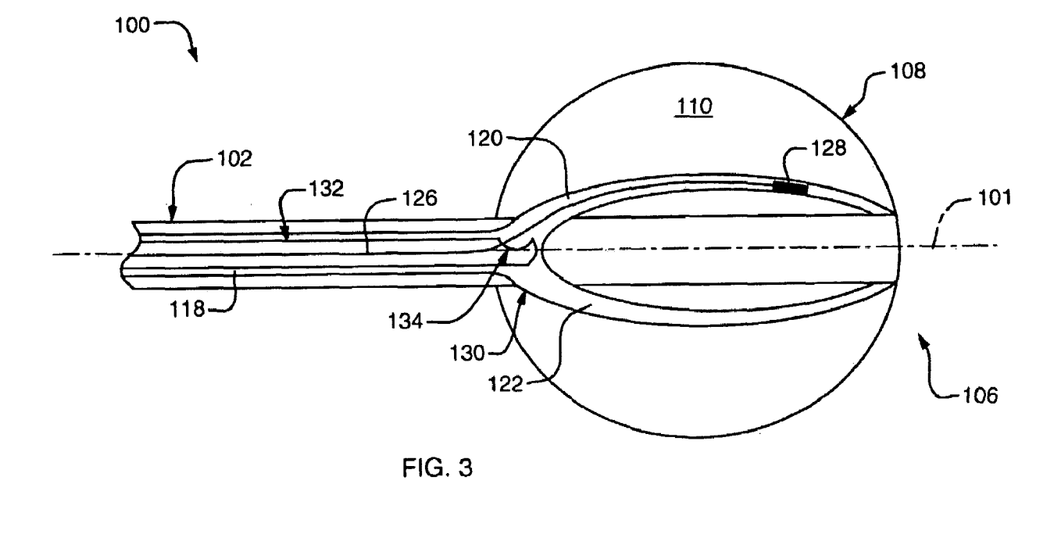
FIG. 3 illustrates a cross-section of an exemplary brachytherapy treatment device having a hollow elongated tubular member disposed within the tubular insertion member.

The number of the plurality of selectable radiation source lumens 120, 122, 124 may vary and, in some embodiments, there may be more than three selectable radiation source lumens 120, 122, 124 and the FIGS. are exemplary only for purposes of clarity of illustration herein. The shape, size, and position of the plurality of selectable radiation source lumens 120, 122, 124 may vary to provide a wide variety of brachytherapy treatment planning options. In some embodiments, there may be two selectable radiation source lumens 120, 122 (as shown in FIGS. 1 & 3). In other embodiments, there may be three (or more) selectable radiation source lumens 120, 122, 124 (as shown in FIG. 2).

The ability to select one of the plurality of selectable radiation source lumens 120, 122, 124 provides a user with a number of different treatment planning options and may be done using a pathway select mechanism. In some embodiments, the pathway select mechanism may simply comprise a radiation source wire 126 (shown in FIG. 3), such as that of a typical afterloader, coupled to the radiation source. The radiation source wire 126 of an afterloader may be both flexible and steerable and thus, may have the ability to be directed down the desired one of the plurality of selectable radiation source lumens 120, 122, 124. A user at the proximal end 104 may control selection of one of the plurality of selectable radiation source lumens 120, 122, 124 at the distal end 106 by steering the radiation source wire 126 into the desired lumen.

In another embodiment, as shown in FIG. 3, the pathway select mechanism may comprise a hollow elongated tubular member 132. The hollow elongated tubular member 132 may be disposed within the tubular insertion member 102. In one embodiment, the hollow elongated tubular member 132 may be disposed within lumen 118 of tubular insertion member and may extend along longitudinal axis 101 between proximal 104 and distal 106 ends of the tubular insertion member 102. The hollow elongated tubular member 132 may have an opening 134 disposed in a wall thereof. The opening 134 may be positionable to correspond to at least one of the plurality of selectable radiation source lumens 120, 122.

Positioning the hollow elongated tubular member 132 may align the opening 134 with at least one of the plurality of selectable radiation source lumens 120, 122 to provide access to at least one of the plurality of radiation source lumens 120, 122. Positioning the hollow elongated tubular member 132 aligns the opening 134 with at least one of the plurality of selectable radiation source lumens 120, 122 to open a pathway to at least one of the plurality of selectable radiation source lumens 120, 122 while closing off at least one other of the plurality of selectable radiation source lumens 120, 122.

FIG. 3 illustrates the aligning of opening 134 with the selectable radiation source lumen 120 to open a pathway to access selectable radiation source lumen 120 while closing off or blocking access to selectable radiation source lumen 122. The radiation source may then be inserted using radiation source wire 126 to insert a radiation source at radiation source position 128. Specifically, the radiation source wire 126 is inserted through main lumen 118, through opening 134 of hollow elongated tubular member 132, and through selectable radiation source lumen 120 to reach radiation source position 128. Because radiation source position 128 is offset from longitudinal axis 101, an asymmetric radiation dosing profile is formed.

While FIG. 3 illustrates one opening 134 for exemplary purposes of illustration, a plurality of openings may be utilized and may be disposed in a number of different positions. In some embodiments, opening 134 may be disposed in a wall, while in other embodiments, opening 134 may be disposed in the distal end 106. The shapes and sizes of the opening 134 may also have any number of configurations. In some implementations, a plurality of different sized openings 134 may be utilized at a number of different positions.

Figure 4:
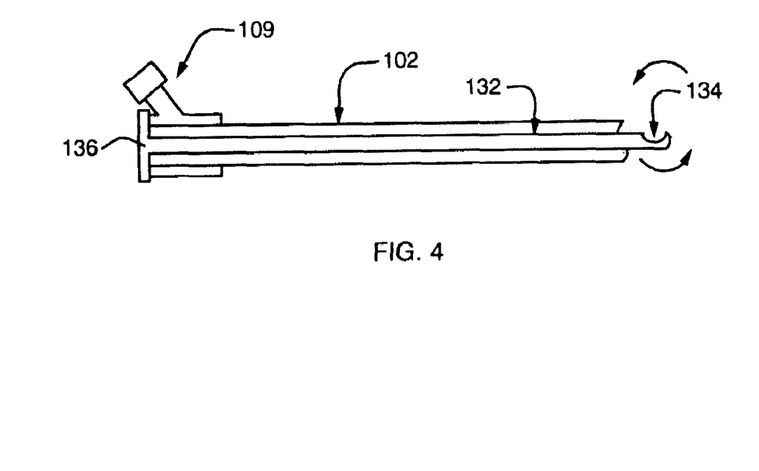
FIG. 4 illustrates a side view of a hollow elongated tubular member disposed within a tubular insertion member (shown partially)

With reference now to FIG. 4, positioning the hollow elongated tubular member 132 within tubular insertion member 102 may comprise rotating (as shown by the arrows). In other embodiments, positioning the hollow elongated tubular member 132 may also comprise sliding, deflecting, or articulating. A user or surgeon at proximal end 104 may control the position of hollow elongated tubular member 132 at distal end 106 using a number of different mechanisms. As shown in FIG. 4, the hollow elongated tubular member 132 may be operably coupled to a thumb wheel 136 positioned on hub 109 at proximal end 104. The thumb wheel 136 may be rotated by a surgeon to rotate hollow elongated tubular member 132 to control positioning of opening 134 to open and/or close one of the plurality of selectable radiation source position lumens 120, 122.

The selectable radiation source lumens 120, 122, 124 are disposed within internal volume 110 and surrounded by expandable member 108 at the distal end 106 of the device 100. As shown in FIGS. 1 & 2, the plurality of radiation source lumens 120, 122, 124 may be disposed to extend substantially parallel to the longitudinal axis 101. However, in other embodiments, the plurality of radiation source lumens 120, 122, 124 may not be disposed substantially parallel to the longitudinal axis 101, and may for example, have a number of different shapes and may be curved to bend or bow further away from longitudinal axis 101 (as shown in FIG. 3).

One or a plurality of selectable radiation source lumens 120, 122, 124 may be disposed along the longitudinal axis 101 or may be offset from the longitudinal axis 101. When it is desirable for the plurality of selectable radiation source lumens 120, 122, 124 to be offset from the longitudinal axis 101, the plurality of selectable radiation source lumens 120, 122, 124 may be positioned or repositioned using a number of different mechanisms. In some embodiments, the plurality of selectable radiation source position lumens 120, 122, 124 may be preformed or prestressed to maintain a particular form or shape, in other embodiments, the offset radiation source position lumens may be deflected, bent, articulated, or otherwise distorted to be offset during treatment. A variety of different catheter deflection mechanisms are disclosed in copending U.S. patent application filed on or about Dec. 18, 2007 and entitled, "Asymmetric Radiation Dosing Devices and Methods for Brachytherapy," which is incorporated by reference herein for all that it discloses.

In some other embodiments, the plurality of offset radiation source lumens 120, 122, 124 may have a number of different configurations, which may change depending upon whether the device 100 is inside or outside of a patient. For example, the plurality of radiation source lumens 120, 122, 124 may be in a compacted configuration with the plurality of radiation source lumens 120, 122, 124 positioned adjacent to the longitudinal axis 101 of the tubular insertion member 102 during insertion to provide a more compact insertion profile for patient comfort. However, once the device 100 is in place, the plurality of radiation source lumens 120, 122, 124 may be deflected, such as via a deflection means, to assume a shape or position slight farther away from the longitudinal axis 101.

As shown in FIGS. 1-3, at least one of the plurality of selectable radiation source lumens 120, 122, 124 may be offset from longitudinal axis 101 to provide an off-center or offset radiation source pathway for placing a radiation source at radiation source position 128. Placing a radiation source at any of the exemplary radiation source positions 128 (shown in FIG. 1) offset from longitudinal axis 101 results in an asymmetric radiation dosing profile, which may be desirable to protect sensitive tissues during treatment. FIGS. 1-3 illustrate several exemplary radiation source positions 128 for clarity herein, but it should be understood that any position in any of the plurality of selectable radiation source pathways 120, 122, 124 may be used as a radiation source position 128.

The issue of protecting sensitive tissues, such as skin, is commonly referred to as skin spacing, and is an important consideration in treatment planning. It may be necessary to ensure sufficient tissue depth exists between sensitive tissues and the radiation source position to prevent damage to the sensitive tissues during treatment. Formation of an asymmetric dosing profile by deflecting the tubular insertion member provides a means for effectively treating areas where tissue depth is minimal between sensitive tissues and the radiation source position.

The radiation dose profile from a radiation source (positioned at radiation source position 128) is typically emitted substantially equally in all 360° surrounding the radiation source position, assuming the radiation source has no abnormalities. Because the radiation dose is emitted substantially equally in all directions, and because it decreases based upon the square of the distance, the proximity of the sensitive tissue (e.g., skin, bone, organs, etc.) to the radiation source 128 results in the skin receiving an undesirably high and potentially very damaging dose of radiation. It is therefore advantageous to protect the sensitive tissue from receiving such a high dose of radiation by positioning the radiation source offset from longitudinal axis 101 to create asymmetric dose profile, which protects the skin while still allowing the remainder of the target tissue to receive a prescribed therapeutic dosage of radiation treatment.

A plurality of exemplary offset selectable radiation source lumens 120, 122, 124 are shown in FIGS. 1, 2, and 3. The use of the offset selectable radiation source lumens 120, 122, 124 reshapes the radiation dosing profile into an asymmetrical radiation dose profile to enable an appropriate dose of brachytherapy treatment to be delivered, even when the treatment site is very close to sensitive tissues. The offset selectable radiation source lumens 120, 122, 124 be slightly offset or more significantly offset, but even a small offset, such between approximately 0.3 mm-2.0 mm, may have a significant impact upon the resulting isodose profile shape.

The offset selectable radiation source lumens 120, 122, 124 may also be used to direct, as well as reshape, the radiation dosing profile to minimize unnecessary exposure to healthy tissue. The asymmetric radiation dosing profile may have a number of different configurations depending upon the particular radiation source used and the positioning, density, and/or radiation absorption properties of the tubular insertion member 102.

The use of a single lumen (i.e., main lumen 118) throughout the body of tubular insertion member 102 keeps the overall size of the device 100 smaller and more flexible, while the use of multiple lumens (i.e., plurality of selectable radiation source lumens 120, 122, 124) provide a wider variety of treatment planning options for creating an asymmetric radiation dosing profile to address skin spacing concerns. The smaller size and flexibility of device 100 help to make patients more comfortable during treatment and ensure incision size remains minimal.

Figure 5:
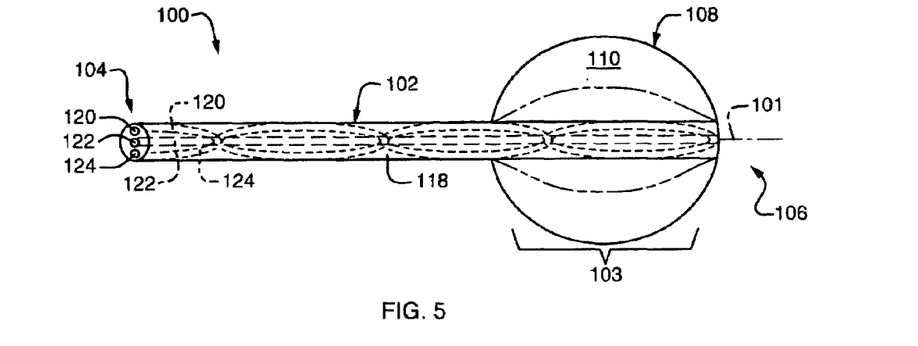
FIG. 5 illustrates a cross-section of an exemplary brachytherapy treatment device having arcuate shaped radiation source lumens.

FIG. 5 illustrates another embodiment of an exemplary brachytherapy treatment device 100. In this embodiment, at least one of the plurality of selectable radiation source lumens 120, 122, 124 may form an arcuate shape with respect to the longitudinal axis 101. The tubular insertion member 102 may comprise a main lumen 118 as well as the plurality of selectable radiation source lumens 120, 122, 124, as shown and described below with respect to FIGS. 7A-7C.

As shown in FIG. 5, the plurality of selectable radiation source lumens may be slightly curved or sloped to form an approximately helical-shaped configuration. The approximately helical-shaped selectable radiation source lumens 120, 122, 124 may be curved around the longitudinal axis 101. The helical-shaped selectable radiation source lumens 120, 122, 124 may be formed in tubular member 102 such as by molding or extrusion processes, wherein the tubular insertion member 102 is turned slightly during the extrusion process. While the selectable radiation source lumens 120, 122, 124 are described herein as approximately helical, they may have any number of curved shapes, including a partially helical shape, such as a sine-wave shape. In some embodiments, only a portion of the plurality of the selectable radiation source lumens 120 may be helical with other portions being non-helical.

The plurality of helical-shaped selectable radiation source lumens 120, 122, 124 are operable to receive and position a radiation source at a number of different radiation source positions along their lengths. The curved or selectable radiation source lumens 120, 122, 124 may be formed in a swirl-like pattern within tubular insertion member 102 providing a multitude of different radiation source positions offset from longitudinal axis 101 to provide a variety of different asymmetrical radiation dosing profiles. As shown in FIG. 5, the selectable radiation source lumens 120, 122, 124 may be selected at proximal end 104. The radiation source may be inserted on a radiation source wire and threaded through the selected radiation source lumens 120, 122, 124 to be positioned at the distal end 106 within expandable member 108.

Figure 6:
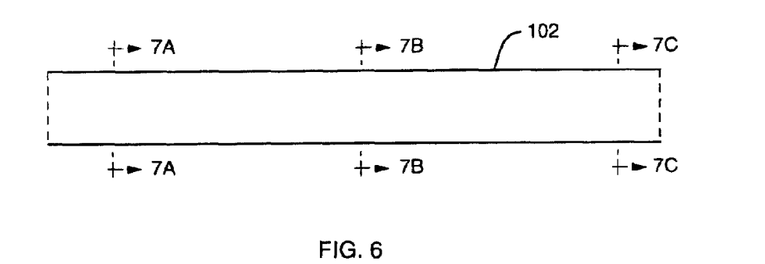
FIG. 6 illustrates a side view of a section of the tubular insertion member of an exemplary brachytherapy treatment device.
Figure 7A:
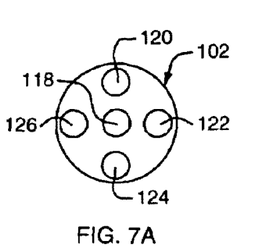
FIG. 7A illustrates a cross-section of FIG. 6 at position A.
Figure 7B:
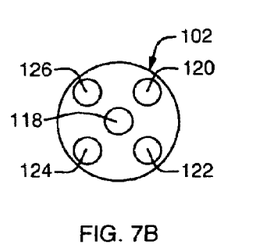
FIG. 7B illustrates a cross-section of FIG. 6 at position B.
Figure 7C:
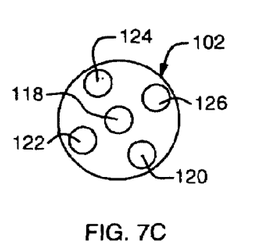
FIG. 7C illustrates a cross-section of FIG. 6 at position C.

FIG. 6 illustrates a side view of a section of an exemplary tubular insertion member 102 comprising a plurality of selectable radiation source lumens 120, 122, 124 having an approximately helical-shape. FIGS. 7A, 7B, and 7C illustrate cross-sectional views of the tubular insertion member 102 of FIG. 6 taken at positions A, B, and C along the tubular insertion member 102. The helical-shaped selectable radiation source lumens 120, 122, 124 may be formed in tubular insertion member 102 by an extrusion process which includes slightly turning or rotating the tubular insertion member 102 during the extrusion process. As shown in FIG. 7A, taken at position A (of FIG. 6), the plurality of selectable radiation source lumens 120, 122, 124, 126 are disposed around main lumen 118. As shown in FIG. 7B, taken at position B (of FIG. 6), the positions of the plurality of selectable radiation source lumens 120, 122, 126 may be rotated slightly, such as in the clockwise direction (the counter-clockwise direction may be also be utilized). As shown in FIG. 7C, taken at position C (of FIG. 6), the positions of the plurality of selectable radiation source lumens 120, 122, 126 may again be rotated slightly, such as in the clockwise direction (the counter-clockwise direction may be also be utilized).

Figure 8:
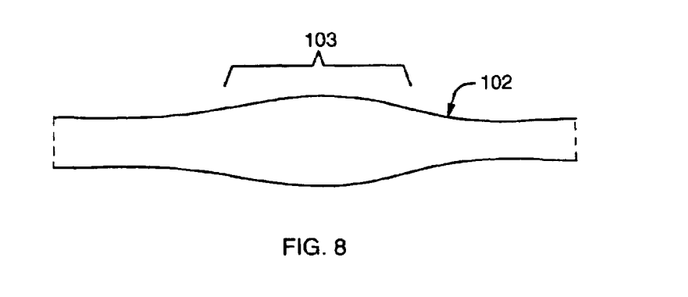
FIG. 8 illustrates a side view of a section of the tubular insertion member of an exemplary brachytherapy treatment device.

With reference now to FIG. 8, the diameter of tubular insertion member 102 may also be varied, as shown by section 103 of FIG. 8 (and in FIG. 5). When the outside diameter of tubular insertion member 102 is increased, the plurality of selectable radiation source lumens 120, 122, 124 within tubular insertion member 102 may be positioned even farther away from longitudinal axis 101, resulting in a larger asymmetric radiation dosing profile with even more treatment options. In some embodiments, only section 103 having a larger diameter may contain approximately helical-shaped radiation source lumens 120, 122, 124 while other sections of tubular insertion member 102 may contain non-helical shaped radiation source lumens 120, 122, 124.

When a plurality of selectable radiation source lumens 120, 122, 124 are utilized, a user may have the ability to select a particular one or a plurality of the selectable radiation source lumens 120, 122, 124 for insertion of a radiation source. The use of a plurality of selectable radiation source lumens 120, 122, 124 and the ability to selectively choose one or more of those selectable radiation source lumens 120, 122, 124 provides a user with a number of different asymmetric radiation dosing profiles providing a variety of different treatment planning options.

Figure 9:
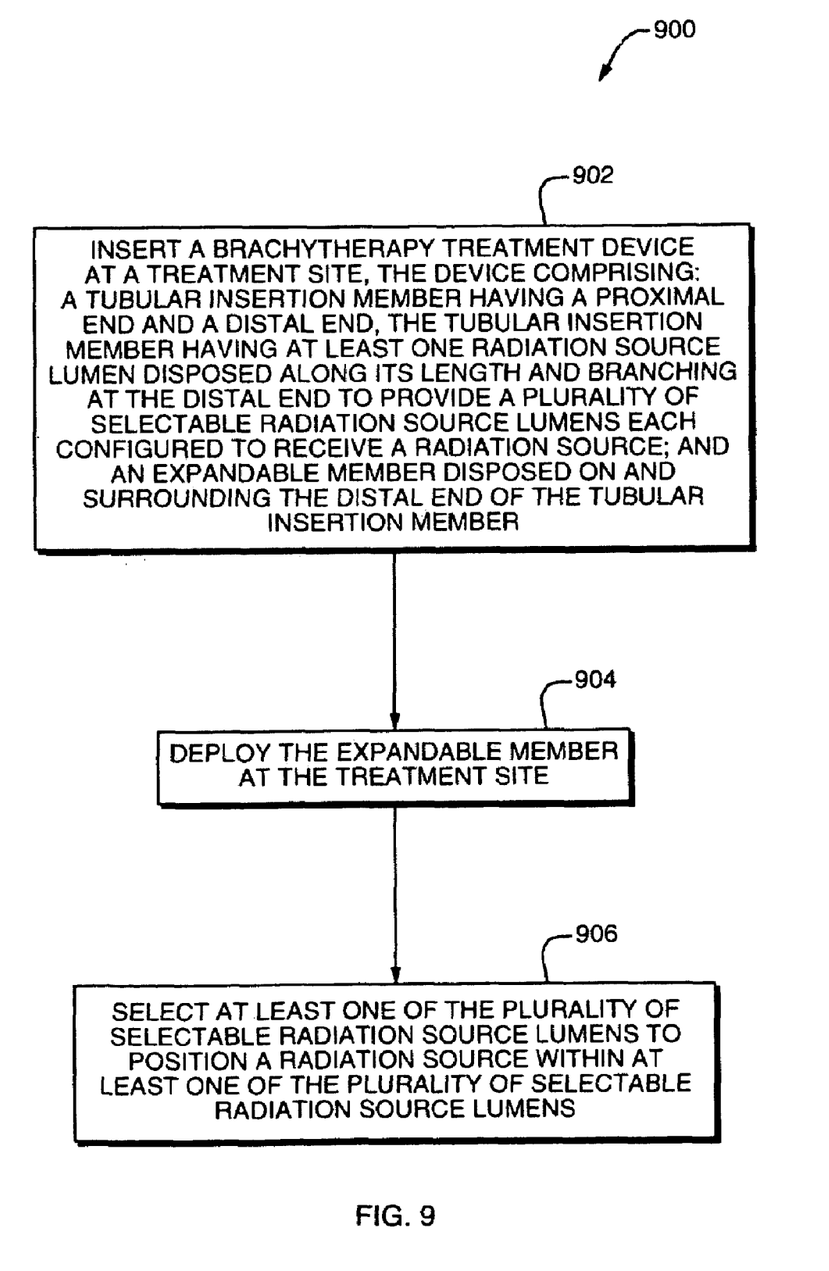
FIG. 9 is a flow-chart illustrating an exemplary method of performing brachytherapy.

Methods for delivering brachytherapy treatment to a treatment site in a patient are also provided herein. One exemplary method 900 of performing brachytherapy treatment may commence with the placement or insertion 902 of a brachytherapy treatment device or catheter 100 (as described in the above embodiments) within a patient at a treatment site. The catheter 100 may comprise a tubular insertion member 102, as previously described above. Prior to placement of the catheter 100, it is common for a surgery to have been performed to remove as much of a tumor as possible. A surgical resection of the tumor is typically performed, leaving a surgical pathway and a resected space or cavity for placement of the catheter within the patient. In some embodiments, the placement of the catheter 100 may include surgically resection, incising, or otherwise altering a patient's tissue.

Once the catheter 100 is appropriately positioned within a patient, one or more expandable members 108 may be deployed 904 or inflated, for example, to fill the cavity of a resected tumor. The tissue surrounding the cavity may substantially conform to the outer surface of the outermost expandable member 108. In this manner, the tissue surrounding the cavity may also be positioned to reshape tissue to ensure a uniform boundary for the radiation dose profile and this may be utilized in conjunction with a deflected tubular insertion member 102 to achieve a predetermined asymmetrical radiation dosing profile.

A method of performing brachytherapy treatment may continue by selecting 906 at least one of the plurality of selectable radiation source lumens 120, 122, 124 to position a radiation source within at least one of the plurality of selectable radiation source lumens. Selecting 906 at least one of the plurality of selectable radiation source lumens 120, 122, 124 may comprise selecting a lumen or pathway offset from a longitudinal axis 101 to create an asymmetric radiation dosing profile at an inner boundary of the treatment site. Selecting 906 may comprise positioning a radiation source wire by steering the radiation source wire through at least one of the plurality of radiation source lumens 120, 122, 124. In some embodiments, selecting 906 may comprise rotating the hollow elongated tubular member 132 to position an opening 134 to correspond to at least one of the plurality of radiation source lumens 120, 122, 124. In this embodiment, selecting 906 may also comprise rotating a thumb wheel 136.

The method then includes placing a radiation source at the radiation source position 128 at the treatment site. When the radiation source is placed the radiation dose profile is reshaped by the deflected shape of the tubular insertion member 102. Following radiation treatment, the catheter 100 may remain within the patient's body in the treatment position so that it can be used during the next treatment session, or it may be removed.

Disclosed herein are devices and methods for use in treating proliferative tissue disorders by the application of radiation, energy, or other therapeutic rays. While the devices and methods disclosed herein are particularly useful in treating various cancers and luminal strictures, a person skilled in the art will appreciate that the methods and devices disclosed herein can have a variety of configurations, and they can be adapted for use in a variety of medical procedures requiring treatment using sources of radioactive or other therapeutic energy. These sources can be radiation sources such as radioisotopes, or man-made radiation sources such as x-ray generators. The source of therapeutic energy can also include sources of thermal, radio frequency, ultrasonic, electromagnetic, and other types of energy.

It should be understood that various changes and modifications to the above-described embodiments will be apparent to those skilled in the art. The examples given herein are not meant to be limiting, but rather are exemplary of the modifications that can be made without departing from the spirit and scope of the described embodiments and without diminishing its attendant advantages.

What is claimed is:

1. A brachytherapy treatment device, comprising:
   a tubular insertion member having a proximal end and a distal end, the tubular insertion member having at least one radiation source lumen disposed along its length and branching at the distal end to provide a plurality of selectable radiation source lumens each configured to receive a radiation source;
   a first expandable member disposed on and surrounding the distal end of the tubular insertion member; and
   a hollow elongated tubular member disposed within the tubular insertion member and having an opening positionable to correspond to at least one of the plurality of selectable radiation source lumens, wherein the hollow elongated tubular member is configured to align the opening with at least one of the plurality of selectable radiation source lumens to provide access to at least one of the plurality of radiation source lumens and the hollow elongated tubular member is configured to rotate with respect to the tubular insertion member.

2. The device of claim 1, wherein at least one of the plurality of selectable radiation source lumens is adapted to position a radiation source offset with regard to a longitudinal axis of the tubular insertion member to form an asymmetric radiation dosing profile.

3. The device of claim 1, wherein the plurality of selectable radiation source lumens at the distal end are offset from a longitudinal axis of the tubular insertion member via a deflection means.

4. The device of claim 1, wherein the plurality of selectable radiation source lumens are adapted to receive a radiation source via a wire, wherein the wire is flexible and steerable from the proximal end to control selection of at least one of the plurality of radiation source lumens at the distal end.

5. The device of claim 1, wherein the hollow elongated tubular member includes a thumb wheel positioned at the proximal end and coupled to the hollow elongated tubular member for rotating the hollow elongated tubular member.

6. The device of claim 1, wherein the hollow elongated tubular member is configured to align the opening with at least one of the plurality of selectable radiation source lumens to open a pathway to at least one of the plurality of selectable radiation source lumens while closing off at least one other of the plurality of selectable radiation source lumens.

7. The device of claim 1, further comprising visualization material disposed within the plurality of selectable radiation source lumens to allow detection of the plurality of selectable radiation source lumens using external imaging.

8. A method of performing brachytherapy, comprising:

inserting a brachytherapy treatment device at a treatment site, the device comprising:

a tubular insertion member having a proximal end and a distal end, the tubular insertion member having at least one radiation source lumen disposed along its length and branching at the distal end to provide a plurality of selectable radiation source lumens each configured to receive a radiation source; and a first expandable member disposed on and surrounding the distal end of the tubular insertion member;

deploying the expandable member at the treatment site; and selecting at least one of the plurality of selectable radiation source lumens to position a radiation source within at least one of the plurality of selectable radiation source lumens, wherein selecting further comprises rotating a hollow elongated tubular member disposed within the tubular insertion member to position an opening in the hollow elongated tubular member to correspond to at least one of the plurality of selectable radiation source lumens, wherein positioning the hollow elongated tubular member aligns the opening with at least one of the plurality of selectable radiation source lumens to provide access to at least one of the plurality of selectable radiation source lumens.

9. The method of claim 8, wherein selecting at least one of the plurality of selectable radiation source lumens comprises selecting a lumen offset from a longitudinal axis to create an asymmetric radiation dosing profile at an inner boundary of the treatment site.

10. The method of claim 8, wherein selecting further comprises positioning a radiation source wire by steering the radiation source wire through at least one of the plurality of selectable radiation source lumens.

11. The method of claim 8, wherein rotating comprises rotating a thumb wheel coupled to the hollow elongated tubular member at the proximal end to rotate the hollow elongated tubular insertion member to position the opening in the hollow elongated tubular member to correspond to at least one of the plurality of selectable radiation source lumens.

12. A brachytherapy treatment device, comprising:

a tubular insertion member having a proximal end and a distal end, the tubular insertion member having at least one radiation source lumen disposed along its length and branching at the distal end to provide a plurality of selectable radiation source lumens each configured to receive a radiation source;

a first expandable member disposed on and surrounding the distal end of the tubular insertion member; and a hollow elongated tubular member disposed within the tubular insertion member and having an opening positionable to correspond to at least one of the plurality of selectable radiation source lumens, wherein the hollow elongated tubular member is configured to align the opening with at least one of the plurality of selectable radiation source lumens to provide access and to open a pathway to at least one of the plurality of radiation source lumens while closing off at least one other of the plurality of selectable radiation source lumens.

13. The device of claim 12, wherein at least one of the plurality of selectable radiation source lumens is adapted to position a radiation source offset with regard to a longitudinal axis of the tubular insertion member to form an asymmetric radiation dosing profile.

14. The device of claim 12, wherein the plurality of selectable radiation source lumens at the distal end are offset from a longitudinal axis of the tubular insertion member via a deflection means.

15. The device of claim 12, wherein the plurality of selectable radiation source lumens are adapted to receive a radiation source via a wire, wherein the wire is flexible and steerable from the proximal end to control selection of at least one of the plurality of radiation source lumens at the distal end.

16. The device of claim 12, wherein the hollow elongated tubular member is configured to rotate with respect to the tubular insertion member.

17. The device of claim 16, wherein the hollow elongated tubular member includes a thumb wheel positioned at the proximal end and coupled to the hollow elongated tubular member for rotating the hollow elongated tubular member.

18. The device of claim 16, further comprising visualization material disposed within the plurality of selectable radiation source lumens to allow detection of the plurality of selectable radiation source lumens using external imaging.

* * * * *